United States Patent
Llewellyn

(10) Patent No.: US 9,648,946 B2
(45) Date of Patent: May 16, 2017

(54) BOTTLE FOR DISINFECTING TOOTHBRUSH

(71) Applicant: Dan Llewellyn, Carlstadt, NJ (US)

(72) Inventor: Dan Llewellyn, Carlstadt, NJ (US)

(73) Assignee: Dan Llewellyn, Carlstadt, NJ (US)

( * ) Notice: Subject to any disclaimer, the term of this patent is extended or adjusted under 35 U.S.C. 154(b) by 0 days.

(21) Appl. No.: 14/598,386

(22) Filed: Jan. 16, 2015

(65) Prior Publication Data

US 2015/0164216 A1    Jun. 18, 2015

Related U.S. Application Data

(62) Division of application No. 13/489,519, filed on Jun. 6, 2012, now Pat. No. 8,974,744.

(60) Provisional application No. 61/520,330, filed on Jun. 8, 2011.

(51) Int. Cl.
| | |
|---|---|
| *A46B 17/06* | (2006.01) |
| *A61L 2/18* | (2006.01) |
| *A46B 9/04* | (2006.01) |
| *B65D 1/04* | (2006.01) |

(52) U.S. Cl.
CPC ............. *A46B 17/065* (2013.01); *A46B 9/04* (2013.01); *A61L 2/18* (2013.01); *B65D 1/04* (2013.01); *A61L 2202/122* (2013.01); *A61L 2202/123* (2013.01); *A61L 2202/16* (2013.01)

(58) Field of Classification Search
CPC .......... A46B 17/065; A46B 9/04; B65D 1/04; A61L 2/18
See application file for complete search history.

(56) References Cited

U.S. PATENT DOCUMENTS

| | | | | |
|---|---|---|---|---|
| 3,342,544 A | * | 9/1967 | Curiel .................. | A61L 2/0005 132/310 |
| 3,347,420 A | * | 10/1967 | Donoghue ............ | G01F 11/286 222/129 |
| 4,418,843 A | * | 12/1983 | Jackman ................ | G01F 19/00 222/158 |
| 4,997,629 A | * | 3/1991 | Marchand ................ | A61L 2/18 137/560 |

(Continued)

FOREIGN PATENT DOCUMENTS

DE         20109877 U1 *  8/2001 ............. A46B 17/06

OTHER PUBLICATIONS

English translation of DE 20109877 U1, Aug. 2001.*

*Primary Examiner* — Regina M Yoo
(74) *Attorney, Agent, or Firm* — Klauber & Jackson LLC

(57) ABSTRACT

A flexible bottle for containing a disinfecting liquid that can be used to disinfect a toothbrush. The bottle has a large reservoir for contain the disinfecting liquid and a small, secondary reservoir that is located proximate to the top of the bottle and which can be filled by squeezing the flexible bottle to force a quantity of the disinfecting liquid into the small, secondary reservoir. There is a cap that is designed to accept a toothbrush for entry into the container and which may have a slot formed therein or flexible flaps. The bottle can, therefore, be filled with disinfecting liquid and a toothbrush introduced into the small reservoir for disinfecting the toothbrush. The disinfecting liquid can then be discarded from the small reservoir and the secondary reservoir refilled as needed by the user.

5 Claims, 3 Drawing Sheets

(56) References Cited

U.S. PATENT DOCUMENTS

| | | | | |
|---|---|---|---|---|
| 5,005,737 A * | 4/1991 | Rohr | ........................ | B65D 1/32 |
| | | | | 137/845 |
| 5,330,081 A * | 7/1994 | Davenport | ............ | G01F 11/286 |
| | | | | 222/207 |
| 5,922,292 A * | 7/1999 | Hecker | .................... | A47K 1/09 |
| | | | | 206/209.1 |
| 6,099,813 A * | 8/2000 | Gipson, II | ................ | A61L 2/18 |
| | | | | 132/308 |
| 6,123,477 A * | 9/2000 | Hecker | .................. | A46B 17/06 |
| | | | | 15/105 |
| 6,253,773 B1 * | 7/2001 | Ingemann | ................ | A47K 1/09 |
| | | | | 132/308 |

* cited by examiner

BOTTLE FOR DISINFECTING TOOTHBRUSH

CROSS REFERENCE TO RELATED APPLICATIONS

This application is a division of U.S. Ser. No. 13/489,519, filed Jun. 6, 2012 which claims the benefit of priority to U.S. Provisional Application No. 61/520,330, filed Jun. 8, 2011, the disclosures of which are herein incorporated by reference in their entireties.

BACKGROUND

The present invention relates to a bottle for disinfecting toothbrushes and, more particularly, to a flexible bottle having an easily filled secondary reservoir for receiving a toothbrush in the secondary reservoir for disinfecting that toothbrush.

With the use of toothbrushes, it is often advantageous to disinfect the cleaning bristles of a toothbrush periodically to maintain the toothbrush clean for use. A typical disinfecting liquid may be a mouthwash, such as Listerine brand mouthwash, and the disinfecting is carried out by immersing the bristles in the disinfecting liquid.

In general, bottles that are available commercially for disinfecting liquids are generally excessively large for the purpose of disinfecting a toothbrush and such bottles, if used to disinfect the toothbrush, are not generally desirable for later use as a supply of mouthwash. As an alternative, the user can pour out a small quantity of the disinfecting liquid into a small container and immerse the toothbrush bristles in that small quantity of liquid, however, it is somewhat inconvenient to have a small container on hand and may result in the user trying to continually locate a suitable container.

Accordingly, it would be advantageous to have a small, secondary reservoir for containing a small, measured amount of the disinfecting liquid normally carried in a large, main reservoir of a bottle in order to use that small, secondary reservoir for disinfecting a toothbrush.

It would be further advantageous that the small, secondary reservoir be actually affixed to or internally located within the larger bottle containing the disinfecting liquid so that the small, secondary reservoir is always available to the user along with the larger bottle.

It would be further advantageous to have a system that would allow the user to selectively fill the small, secondary reservoir with disinfecting liquid from the large, main reservoir, just prior to use and then allow the user to discard that used disinfecting liquid so that a fresh quantity of disinfecting liquid can be available to continually fill the small, secondary reservoir when needed.

SUMMARY OF THE INVENTION

Accordingly, the present invention overcomes the aforesaid problems and difficulties by providing a bottle for disinfecting a toothbrush that comprises a flexible container that forms a main reservoir where the liquid, such as a disinfecting liquid is contained. The flexible container has a top with a removable cap that seals an opening in the top and may be affixed to the top by means a screw threaded connection.

There is a secondary reservoir located proximate to the top of the container and that secondary reservoir is sized so as to hold a relatively small quantity of the disinfecting liquid sufficient for immersion of the bristles of a toothbrush. The secondary reservoir may be situated within the flexible container or may be exterior thereof. The secondary reservoir may have measured graduations that can be imprinted on the secondary reservoir to enable the user to accurately, visually determine the quantity of the disinfecting liquid held within the secondary reservoir.

A passageway is formed between the main reservoir and the secondary reservoir and, like the secondary reservoir, the passageway may be contained within the flexible container or exterior to the flexible container. As such, by simply squeezing the flexible container, the disinfecting liquid is forced from the main reservoir to the secondary reservoir where it is available for disinfecting a toothbrush.

Thus, the secondary reservoir can be filled and emptied according to its use in disinfecting a toothbrush without contaminating the disinfecting liquid contained in the main reservoir and there is a ready supply of fresh disinfecting liquid that can easily be pumped from the main reservoir to the secondary reservoir to replenish or refill the secondary reservoir.

These and other features and advantages of the present invention will become more readily apparent during the following detailed description taken in conjunction with the drawings herein.

DETAILED DESCRIPTION OF THE INVENTION

Figure 1:
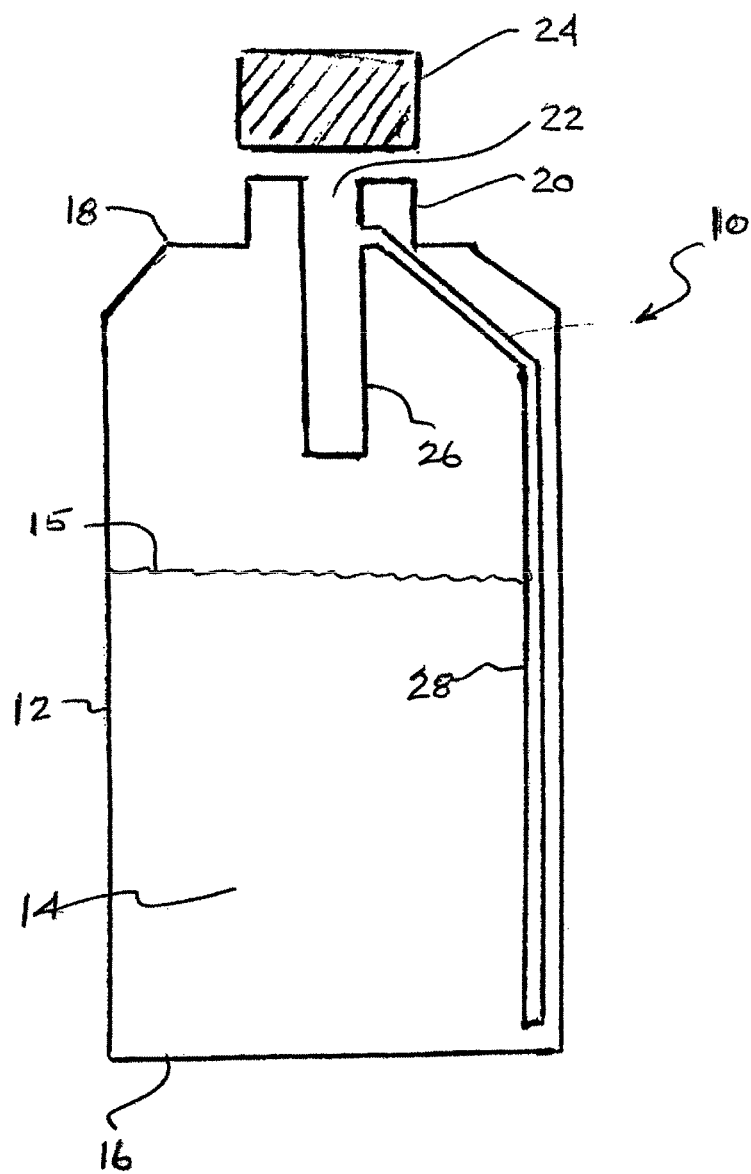
FIG. 1 is a side view of a bottle constructed in accordance with the present invention.

Referring now to FIG. 1, there is shown a side view of the bottle 10 of the present invention. As can be seen, the bottle 10 comprises a flexible container 12 forming therein a main reservoir 14. The main reservoir 14 is liquid tight and is adapted to contain a quantity of a disinfecting liquid 15, such as a mouthwash.

The bottle 10 has a closed bottom 16 and a top 18 where there is a threaded lip 20 forming an opening 22. A cap 24 is threaded to the threaded lip 20 to cover and uncover the opening 22. A secondary reservoir 26 is located proximate to the top 18 internal of the flexible container 12 and the opening 22 leads into the secondary reservoir 26 to provide access to the secondary reservoir 26 when the cap 24 is removed. There is also a passageway 28 that communicates between the main reservoir 14 and the secondary reservoir 26. The secondary reservoir 26 can be comprised of a molded plastic material and may be molded, such as by blow molding, along with the flexible container 12 or molded separately and affixed to the interior of the flexible container 12. The passageway 28 may be a flexible plastic tube.

In any event, it can be seen that by removing the cap 24, the flexible container 12 can be squeezed by a user to force a quantity of the disinfecting liquid 15 from the main reservoir 14 upwardly and into the secondary reservoir 26.

As such, the secondary reservoir 26 can be readily filled with the disinfecting liquid upon the desire of a user.

At this point, the disinfecting liquid contained within the secondary reservoir 26 is accessible through the opening 22 so that a toothbrush can be inserted into the secondary reservoir 26 to disinfect that toothbrush.

If the user wants to access the contents of the main reservoir 14 to use the disinfecting liquid for purposes of a mouthwash, the secondary reservoir 26 may be filled as described and the contents poured from the secondary reservoir 26 into another container or used in a normal manner. If a large amount of the disinfecting liquid is desired to be removed for the bottle 10, the secondary reservoir 26 may be filled by squeezing the flexible container 12 and filing the secondary reservoir 26 multiple times and, each time, pouring the contents of the secondary reservoir 26 outwardly through the opening 22.

As can be seen, when the secondary reservoir is being filled with the disinfecting liquid 15 form the main reservoir 14, the cap 24 must be removed to open the secondary reservoir 26 to the atmosphere.

Figure 2:
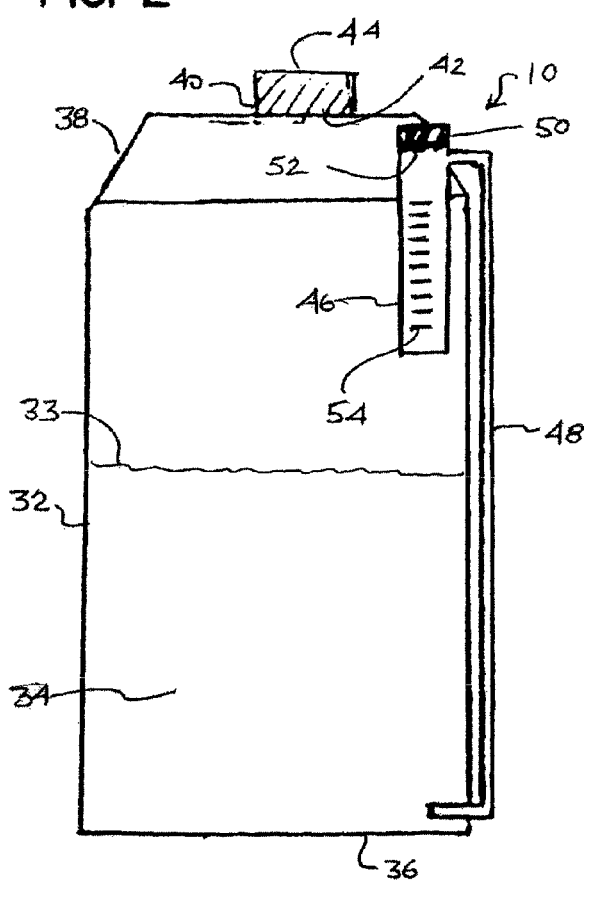
FIG. 2 is front view of an alternate exemplary embodiment of the bottle of the present invention.
Figure 3:
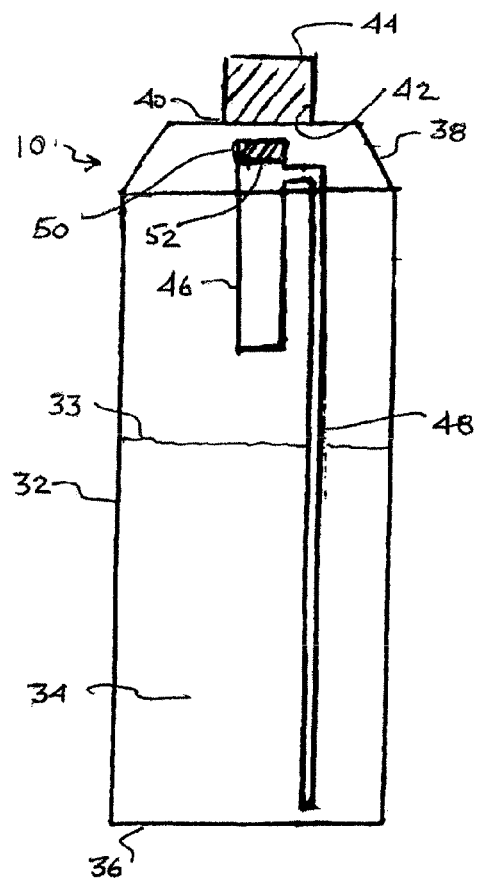
FIG. 3 is a side view of the embodiment of FIG. 2.

Turning then to FIGS. 2 and 3, there is shown a front view and a side view, respectively, of an alternate exemplary embodiment of the present invention wherein there is also a bottle 10 comprised of a flexible container 32 for containing a disinfecting liquid 23 within a main reservoir 34 having a bottom 36 and a top 38. Again, there is a threaded lip 40 forming an opening 42 covered by a removable cap 44.

In this embodiment, however, the secondary reservoir 46 is located external of the flexible container 42 and, as can be seen, passageway 48 passes through the flexible container 32 to the exterior thereof and then extends along the exterior of the flexible container 32 to the secondary reservoir 46 such that when the flexible container 30 is squeezed by a user, the disinfecting liquid passes along the exterior of the flexible container 32 to the secondary reservoir 46 that is located on the exterior of the flexible container 32. In this embodiment, therefore, there is a secondary cap 50 that closes the open end 52 of the secondary reservoir 46.

With this embodiment, when the secondary cap 50 is removed from the secondary reservoir 46 to open the secondary reservoir 46, and the removable cap 44 is closed, the flexible container 32 can be squeezed to force the disinfecting liquid 33 from the main reservoir 34 up and into the secondary reservoir 40. Alternatively, if the user desires to remove the contents of the bottle 10, the secondary cap 50 can be affixed in its closed position and the removable cap 44 removed. The disinfecting liquid 33 can then be simply poured out of the opening 42 formed in the top 38 of the flexible container 32 in the normal manner.

In either of the embodiments of FIG. 1 and FIGS. 2 and 3, there can also be measured graduations 54 present on the secondary reservoir 46 (shown only in FIG. 2) so that the user can accurately determine the precise measure of liquid in the secondary reservoir 46 for the correct dosage of the disinfecting liquid or to be used to measure out a precise quantity of the disinfecting liquid for use.

Figure 4:
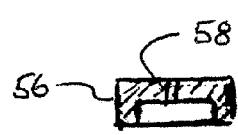
FIG. 4 is a side cross-sectional view of a cap that is usable with the present invention.
Figure 5:
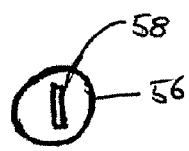
FIG. 5 is a top view of the cap of FIG. 4.

Turning then to FIGS. 4, and 5, taken along with FIGS. 1-2, there is shown a side cross sectional view and a top view of a cap 56 that can be used with the present invention. As can be seen, the cap 56 has a rectangular slit 58 formed therein for the introduction of a toothbrush therethrough. The cap 56 can be used to replace cap 24 of the FIG. 1 embodiment, that is, as the main cap of the flexible container 12.

As such, the bottle 10 can be sold with a normal sealed cap so as to prevent leakage from the bottle 10 during handling in a store and then a cap 56 having a slit 58 can replace the normal cap in the household so that a toothbrush can be inserted into the bottle 10 with a minimum of leakage since the rectangular slit 58 can be dimensioned so as to create a snug fit between the rectangular slit 58 and a toothbrush handle. Alternatively, instead of a rectangular slit 58, the cap 56 may have flexible flaps to allow entrance of a toothbrush while forming a seal against the toothbrush handle.

The cap 56 can also be used as the secondary cap 50 of the FIG. 2-3 embodiment under the same conditions.

Figure 6:
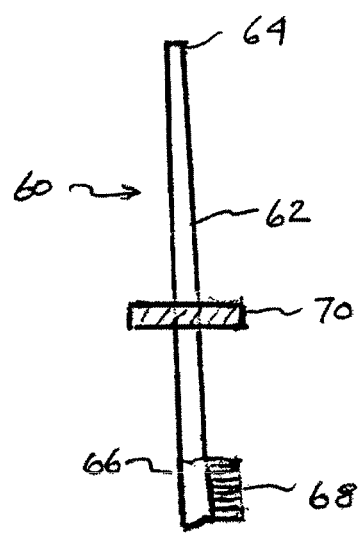
FIG. 6 is a side view of a toothbrush that can be used with the present invention.

Turning finally to FIG. 6, there is a side view of a toothbrush 60 that can be used with the present invention. The toothbrush 60 comprises a handle 62 having a proximal end 64, a distal end 66 and a set of bristles 68 located at the distal end 66.

There is a sealing member 70 located between the proximal end 64 and the distal end 66 of the handle 62 and which is firmly affixed to or molded with the handle 62 of the toothbrush 60. That sealing member 70 can be a sealing plug that allows the toothbrush 60 to be inserted into an open end of one of the secondary reservoir of FIGS. 1-3 so that the toothbrush 60 is effectively sealed within in a secondary reservoir.

Alternatively, the sealing member 70 may be a cap having screw threads that can be screwed into the flexible container 12 of FIG. 1 or the secondary reservoir 46 of the FIG. 2-3 embodiment and affix the bristles 68 of the toothbrush 60 in the disinfecting liquid contained within the secondary reservoir 46. With the latter embodiment, the toothbrush 60 may be sold commercially already affixed to the bottle 10 and contained within a secondary reservoir.

As an advantage of the FIG. 6 embodiment, the secondary reservoir can be sealed to prevent dust or dirt from entering into the secondary reservoir and the sealing member 70 prevents the disinfecting liquid in the secondary reservoir from evaporating. As a further advantage a company can combine the manufacture and marketing of a toothbrush with a mouthwash product and take advantage of the possibility of bundling the two products together to achieve a commercial advantage and beneficial savings to the consumer.

As can now be seen, the present flexible container can be readily blow molded in conventional manner by an alteration of the current molds and no additional assembly or production steps need to be taken, other than adding an additional cap for the FIG. 2-3 embodiment. Since the bottle of the present invention can be produced with the same bottle dimensions as current bottles not having a secondary reservoir, there also need be no change to present shipping cartons. It is noted that the incorporation of the secondary reservoir may, however, slightly reduce the quantity of mouthwash contained in a bottle since some of the volume of the mouthwash in a container is taken up by the presence of the secondary reservoir in the FIG. 1 embodiment.

Those skilled in the art will readily recognize numerous adaptations and modifications which can be made to the toothbrush disinfecting bottle and its use of the present invention which will result in an improved bottle and method of its use, yet all of which will fall within the scope and spirit of the present invention as defined in the following claims. Accordingly, the invention is to be limited only by the following claims and their equivalents.

What is claimed is:

1. A method of disinfecting a toothbrush comprising the steps of:
providing a bottle comprising a flexible container forming a main reservoir containing a disinfecting liquid, the flexible container having a top having a first opening, a cap removably covering the first opening at the top of the flexible container, wherein the cap has a second opening having flexible lips allowing a toothbrush to pass therethrough, and a secondary reservoir located proximate to the top of the flexible container wherein the secondary reservoir has a third opening having a second cap affixed thereto, wherein the second cap has a rectangular opening for allowing a toothbrush to pass therethrough, and a passageway leading from the main reservoir to the secondary reservoir,
squeezing the flexible container to force the disinfecting liquid from the main reservoir to the secondary reservoir, and
inserting a toothbrush through the rectangular opening into the third opening to enter the secondary reservoir for contacting the toothbrush with the disinfecting liquid contained therein.

2. The method of claim 1 wherein the step of inserting a toothbrush through the rectangular opening into the third opening to enter the secondary reservoir includes the step of sealing a third opening.

3. The method of claim 1 wherein the-secondary reservoir is external.

4. The method of claim 1 wherein the step of squeezing the flexible container comprises squeezing the flexible container to force the disinfecting liquid through the passageway internal of the flexible container.

5. The method of claim 1 wherein the step of squeezing the flexible container comprises squeezing the flexible container to force the disinfecting liquid through the passageway external of the flexible container.

* * * * *